United States Patent [19]

Barsotti et al.

[11] Patent Number: 4,791,915
[45] Date of Patent: Dec. 20, 1988

[54] ULTRASOUND THERAPY DEVICE

[75] Inventors: Edward J. Barsotti, Batavia; Richard D. Hance, Elburn, both of Ill.

[73] Assignee: Dynawave Corporation, Geneva, Ill.

[21] Appl. No.: 70,608

[22] Filed: Jul. 2, 1987

Related U.S. Application Data

[63] Continuation-in-part of Ser. No. 912,566, Sep. 29, 1986, abandoned.

[51] Int. Cl.⁴ .............................................. A61H 1/00
[52] U.S. Cl. ................................................. 128/24 A
[58] Field of Search ............... 128/24 A, 660; 604/22, 604/43

[56] References Cited

U.S. PATENT DOCUMENTS

| | | | |
|---|---|---|---|
| 4,109,643 | 8/1978 | Bond et al. | 128/666 |
| 4,368,410 | 1/1983 | Hance et al. | 128/24 A |
| 4,583,529 | 4/1986 | Briggs | 128/24 A |
| 4,587,958 | 5/1986 | Noguchi et al. | 128/24 A |
| 4,708,127 | 11/1987 | Abdelghani et al. | 128/24 A |

OTHER PUBLICATIONS

"Sonopuls 434" brochure by Enraf Nonius, No. 1.7.3 E, date unknown.

"Sonicator" brochure by Mettler Electronics, date unknown.

"Amrex Electro-Therapy Instruments" brochure by Amrex-Zetron, Inc., catalog 883/20K, date unknown.

"A New Generation of Amrex Combination Therapy" brochure by Amrex-Zetron, Inc., date unknown.

Hartl, J. et al., International Application #PCT/HU81/00019 Intl. Publn. No. WO 82/03779 Publ. 11 Nov. 1982.

Frederick, J. "Ultrasonic Engineering," John Wiley & Sons, 1965 pp. 109-115, 346-349.

Primary Examiner—Francis J. Jaworski
Attorney, Agent, or Firm—Hill, Van Santen, Steadman & Simpson

[57] ABSTRACT

An ultrasound therapy device has a hand-held transducer connected to a base unit having a front display and control panel. A control circuit within the base unit is microprocessor-based and enables an operator to select various output modes, intensities and durations. Transducer current, voltage, and phase angle are monitored for servo control, coupling detection, and fault protection of the output from an efficient power amplifier. Among the front panel displays is a percentage of coupling bar graph.

21 Claims, 10 Drawing Sheets

ULTRASOUND THERAPY DEVICE

This is a continuation-in-part of application Ser. No. 912,566, filed Sept. 29, 1986, and now abandoned.

BACKGROUND OF THE INVENTION

1. Field of the Invention

The present invention relates to a device for applying ultrasound energy to a patient for therapy in either a continuous or a pulsed mode.

2. Description of the Prior Art

Ultrasound applicator devices are known for transmitting either continuous or pulsed ultrasound energy, such as to the body of a patient for treatment of various maladies. In our earlier U.S Pat. No. 4,368,410, assigned to the same assignee as is the present invention, a servo feedback loop measures actual power delivered to a transducer to adjust the output as loading conditions at the transducer change. The changing load conditions are a result of the different absorption of ultrasound energy by different types of tissue, as well as of changing degrees of coupling between the transducer and the patient's body. The servo feedback is provided by supplying signals representative of voltage and current at the transducer to an analog multiplier to maintain the output power to the transducer at the selected level. The device enables the operator to select not only a pulse period, but also a pulse duration through front panel touch pad switches.

It is also known to provide ultrasound devices with interchangeable transducer heads although recalibration is required, devices that operate at more than one ultrasound frequency, and ultrasound devices that interrupt the output when the transmitted ultrasound energy falls below a predetermined level.

SUMMARY OF THE PRESENT INVENTION

Clear and easy-to-read displays, including a percent of coupling display, are provided in an ultrasound therapy device of the present invention having a highly efficient output amplifier and a processor-directed digital control circuit. Output coupling is monitored by the processor so that output power levels can be corrected, overheating prevented, and system faults detected.

Generally, the present ultrasound device includes a hand-held transducer/applicator having an ultrasound energy emitting face for placement against and movement over a patient's body. As the ultrasound energy from the transducer is coupled into the tissue of the patient, a therapeutic effect results. The transducer/applicator is connected by a flexible cable to a base unit having a front panel on which are numerous displays and controls. An operator of the ultrasound device is able to preset the treatment time, the output intensity and the pulse mode by manipulating the front panel controls, and to monitor such functions visually and audibly during treatment sessions. Most notably, the operator is able to observe the coupling efficiency between the transducer and the patient by the coupling display, which is preferably in the form of an easy-to-read bar graph.

The control circuit for the present device is microprocessor-based for improved control and monitoring of all functions. The control circuit monitors transducer voltage and current, as well as the phase angle therebetween to provide servo control for varying tissue loads which result from differing tissue densities. In another embodiment, servoing is provided through software by a signal proportional to the square of the power amplifier power supply voltage and/or current. Such monitoring also enables the microprocessor to prevent overheating by reducing power to the transducer during poor tissue coupling, as well as to trigger a shut down upon detection of an electrical fault. The treatment timer is suspended for the duration of the output reduction so that the selected dose is received. Upon restoration of coupling to the patient, power to the transducer is brought back to the selected level. When the shut down is a result of an electrical fault, both a visual and an audio indicator are conveyed to the operator.

The efficiency of the present device is high, in part because of correction of the transducer's power factor to operate midway between series and parallel resonance. Also, the power amplifier for driving the transducer is an efficient switching amplifier that produces a square wave output. Thus, both the transducer and the amplifier run cool, eliminating the need for fans and the like and also increasing the reliability.

Other features include an automatic self-test when power is turned on and the provision of a radio frequency shield between secondary windings of the power transformer, along with a transformer thermal cut off.

Thus, the present therapy device permits an operator to accurately control the application of ultrasound energy in a safe and well-informed manner, while insuring effective treatment and efficient operation.

DESCRIPTION OF THE PREFERRED EMBODIMENTS

Figure 1:
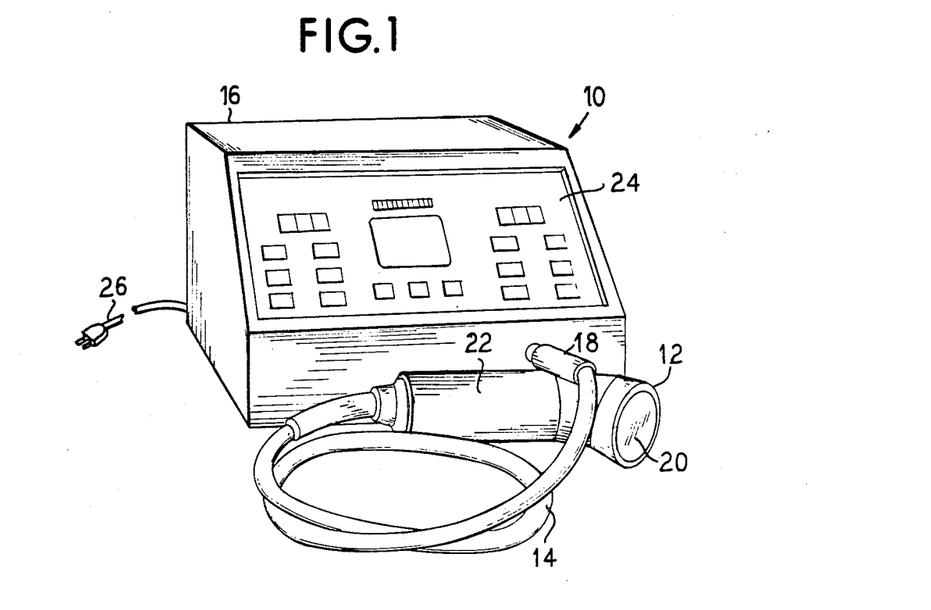
FIG. 1 is a perspective view of a therapeutic ultrasound device according to the principles of the present invention.

In FIG. 1, a therapeutic ultrasound device is shown generally at 10 for the medical application of ultrasound energy to a patient. The device 10 includes a hand-held transducer 12 connected by a cable 14 to a base unit 16. The cable 14 is removably connected to the base unit 16 by a connector plug 18 so that replacement of the transducer 12 is possible. The transducer 12 has an ultrasound energy emitting face 20 disposed at an angle to a handle portion 22, which is gripped by the therapist or operator. A front control panel 24 is provided at an angle for easy access by the operator and includes a plurality of display and control means for controlling the transmission of ultrasound energy from the transducer 12. A power cord 26 is also provided for the base unit 16 by which the device 10 is connected to a standard electrical outlet.

Figure 2:
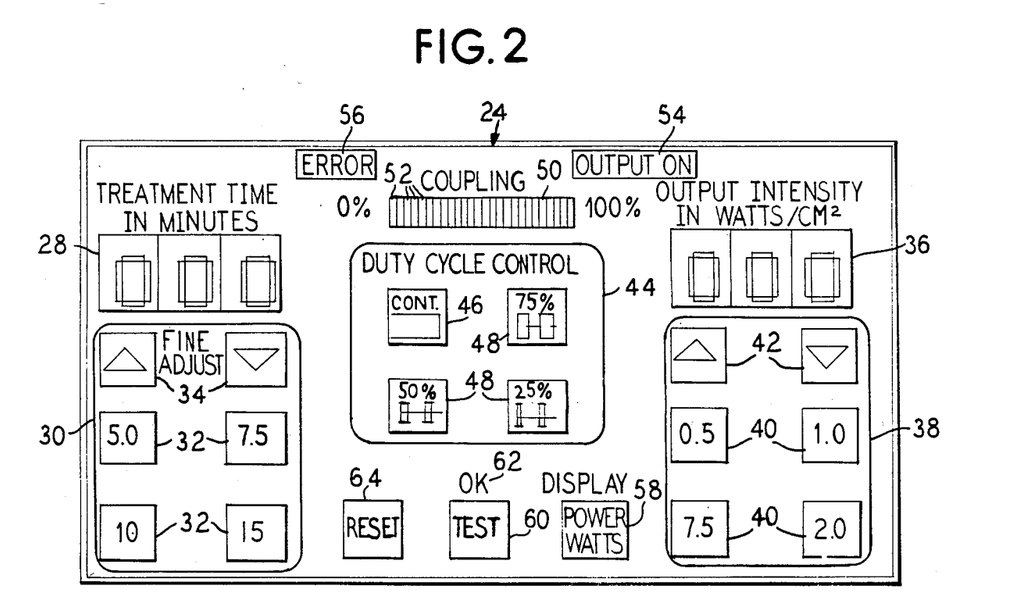
FIG. 2 is an elevational view of the front panel of the device shown in FIG. 1.

With reference to FIG. 2, one embodiment of a control panel 24 is shown therein, including a treatment time display 28 and treatment time controls 30 by which the desired number of minutes for treatment is selected. Individual selection buttons or switches 32 are included in the treatment time control 30 for selection of the more popular time settings. Fine up and down adjustment switches 34 are also included for selecting time intervals not represented by an individual switch 32. The treatment time display 28 is preferably a numeric display, such as seven segment numeric LED or LCD displays.

The display panel 24 also includes an output intensity display 36, also preferably a numeric display, which displays the ultrasound energy output in watts per square centimeter. An output intensity control 38 has individual selection switches 40 for setting predetermined intensity values as well as fine adjust switches 42 for selecting other intensity values.

A duty cycle control 44 enables an operator to select either a continuous output waveform or a pulsed output waveform of various duty cycles. In the illustrated embodiment, an operator may select a continuous duty cycle by depressing switch 46 or may select one of three pulsed duty cycles of 25%, 50%, or 75% by operating a corresponding one of the switches 48.

By selecting a treatment time, an output intensity, and a duty cycle, after power up of course, the unit begins operating to transmit ultrasound energy from the transducer 12. The present invention senses the amount of the supplied power which is actually transmitted to the patient and displays the transmitted, or coupled, power as a percentage or fraction of the maximum available ultrasound power by a coupling indicator 50. The coupling indicator 50, in the preferred embodiment, is a light bar which indicates coupling efficiency from 0% to 100% so that the operator gets a visual clue of the amount of ultrasound power actually being received by the patient. The operator can thereby quickly determine if the transducer 12 is properly applied and thereafter make adjustments. The light bar coupling display 50 of one embodiment includes 16 LEDs 52 connected to form the individual illuminated segments of the bar graph 50.

Additional controls and displays on the front panel 24 include an output on indicator 54 to show when ultrasound energy is being delivered to the transducer 12 and an error indicator 56 to indicate a machine fault, such as a short circuit or a broken cable, resulting in the unit 10 being automatically shut down. A display power watts switch 58 is operable to change the output intensity display 36 to a display of total output power in watts. When the display watts switch 58 is released, the display 36 reverts back to a display of intensity in watts per square centimeter. Another switch is the test switch 60 which is manipulated to initiate a self-test of the microprocessor memory circuits and the displays on the front panel 24 of the unit 10, the results thereof being displayed by an OK indicator 62. By maintaining the test switch 60 in a depressed condition, a transducer tuning control can be adjusted until properly tuned as indicated by the coupling indicator 50. A reset control 62 is also provided by which the control circuitry can be placed in a known state. The control switches on the front panel 24 are preferably formed by touch pad switches, although other control means may also be used. Likewise, the displays may instead be other display means.

Figure 3:
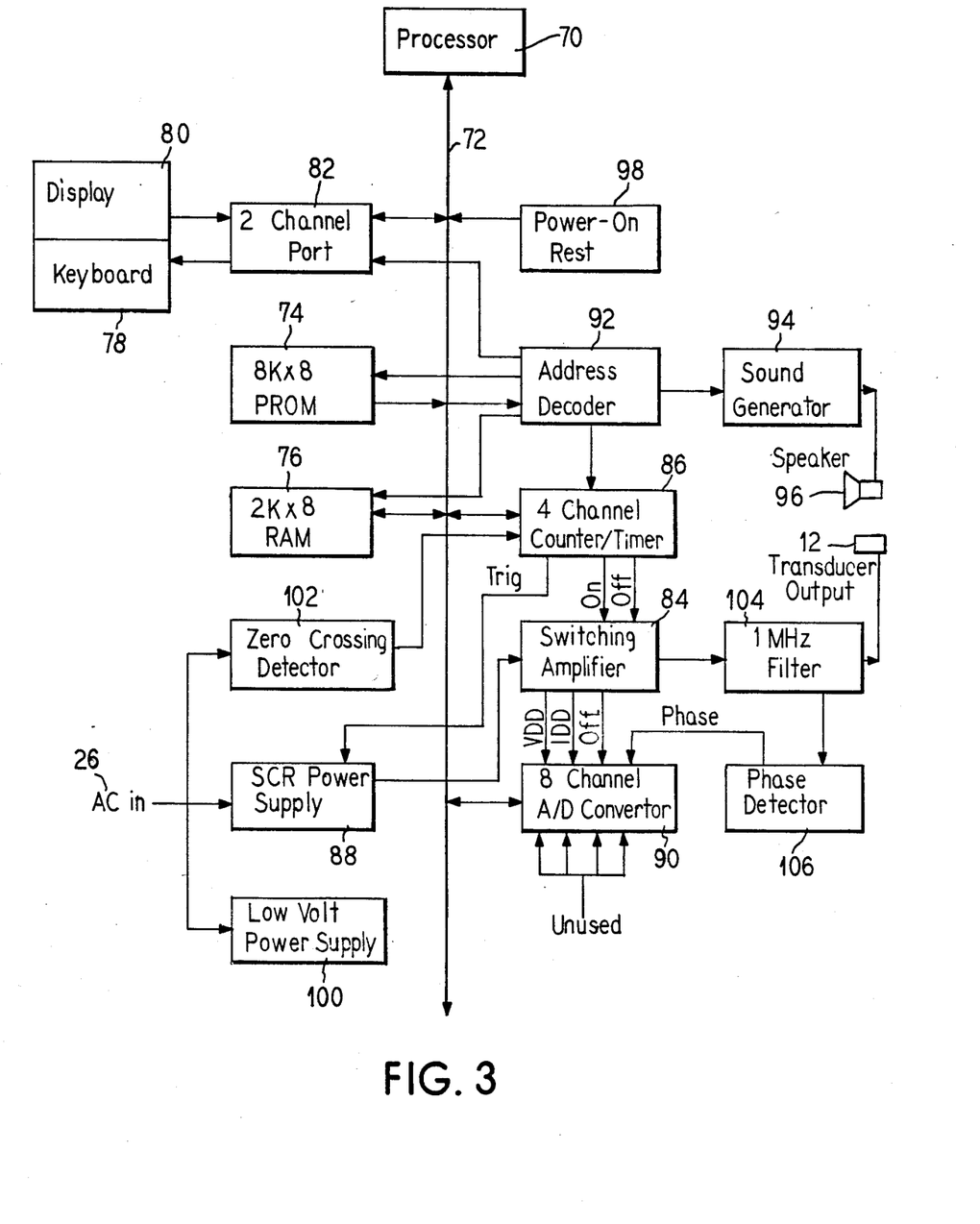
FIG. 3 is a functional block diagram of the control circuitry for the ultrasound device of the present invention.

In FIG. 3, a functional block diagram of the control circuitry for the ultrasound therapy device 10 includes a microprocessor 70 linked by a non-multiplexed address, data, and control bus 72 to a variety of peripheral and control devices. The microprocessor 70 of a preferred embodiment is a four MHz. eight bit Z80 microprocessor. The microprocessor operates under the control of a program stored in an 8 K by 8 bit PROM 74, and utilizes a 2 K by 8 bit RAM unit 76 for storage of information and variables as needed. The program, among other things, enables the microprocessor 70 to provide servoing of the ultrasound output. A keyboard 78 and a display 80 provide a communication link between the user and the microprocessor 70 through a dual eight-bit parallel input/output port (I/O) 82. The keyboard display blocks 78 and 80 are the equivalent of the front panel 24 controls and displays.

The microprocessor 70 switches an ultrasound power amplifier 84 on and off through a four-channel counter/timer circuit (CTC) 86. An SCR power supply 88 supplies the high voltage for the power amplifier 84. The SCR power supply 88 is controlled by a trigger pulse from the counter timer circuit 86. An eight channel analog-to-digital (A/D) converter 90 monitors the device parameters, i.e. amplifier voltage, current, phase, and status, for transmittal to the microprocessor 70.

Other functional blocks shown for the control circuit include an address decoder 92 by which the microprocessor 70 accesses information in the memories 74 and 76, as well as information transmitted and received through the I/O port 82, by select lines from the decoder 92 to the other circuits. The address decoder 92 is connected to operate a sound generator 94 which feeds an audio output 96, such as a speaker, to alert the operator to changes in the unit's functions. A power-on reset block 98 provides a means for not only switching the unit 10 on, but also for automatically placing the circuit in a known state by transmitting a common reset signal.

The AC power signal is received at the AC input 26 and fed not only to the SCR power supply 88, but also to a low voltage power supply 100, which in turn supplies power to the balance of the control circuitry. A zero crossing detector 102 likewise receives the AC power signal and outputs pulses corresponding to the zero axis crossings of the sinusoidal input. The pulses from the zero crossing detector 102 are transmitted to the four channel counter timer circuit 86 that then initiates a delay before a trigger signal is sent to the SCR power supply 88. By varying the delay between the zero axis crossing and the triggering of the SCR power supply 88, the amplitude of the AC signal at which the SCR 88 is triggered changes. This enables the amplitude of the SCR output to be varied. The switching amplifier 84, which is driven by the SCR power supply 88, transmits its ultrasonic signal through a one MHz. filter 104 to the transducer 12. The amplitude of the amplifier signal varies as the SCR signal varies. The filtered one MHz. signal at the transducer is monitored by a phase detector 106 which feeds a phase signal to the A/D converter 90 for use by the microprocessor 70 in feedback or servo control of the ultrasound output. Through software utilized in the microprocessor 70, the phase signal in conjunction with a voltage or current signal from the power amplifier power supply is used for servo control of either the preset output power or the output intensity.

Figure 4A:
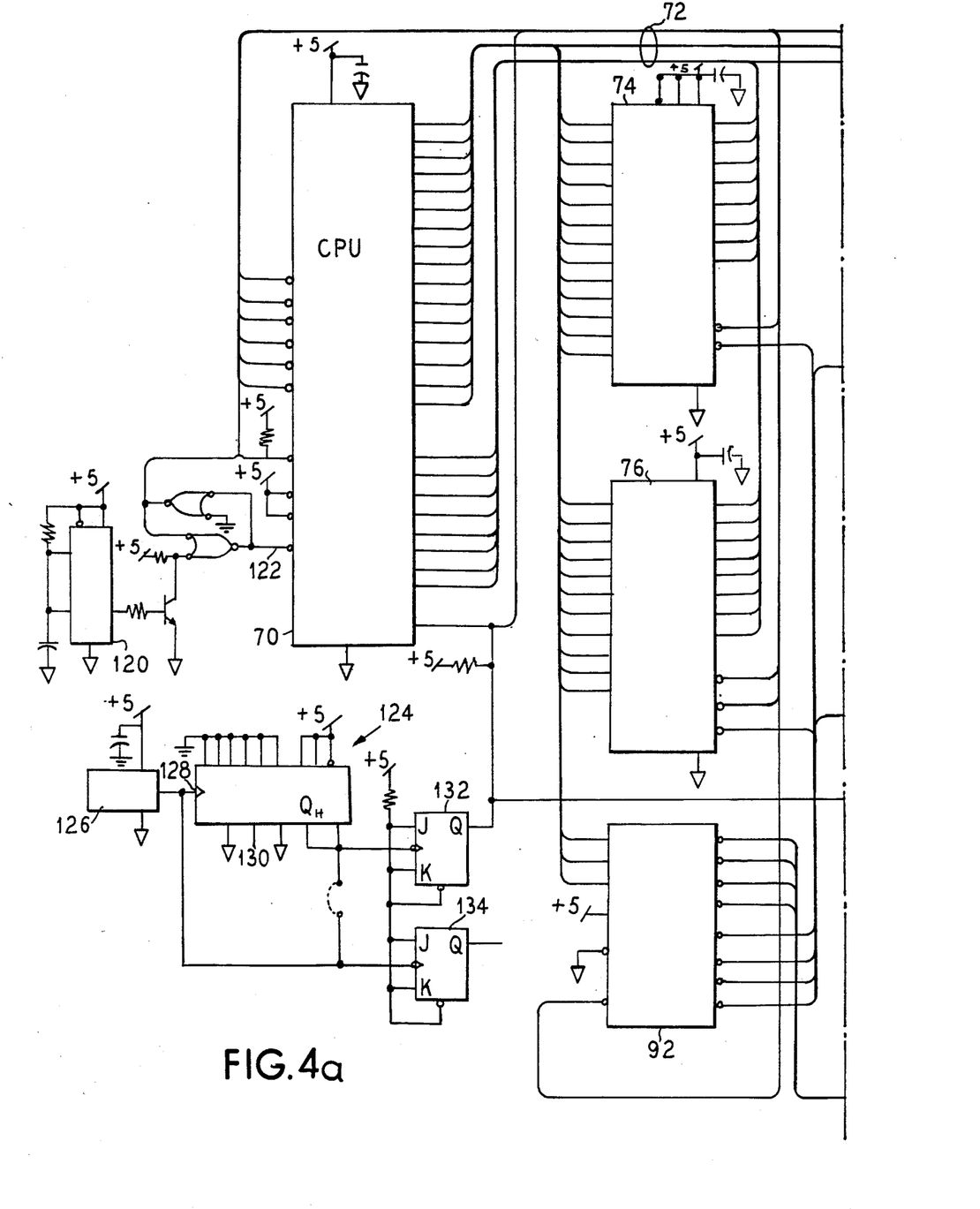
FIGS. 4 through 9 are circuit diagrams of one embodiment of a control circuit for use in the ultrasound device of the present invention.

In FIG. 4a, the circuit is shown in more detail, including the processor or CPU 70 connected to the PROM 74, the RAM 76, and the address decoder 92 by the bus 72. The CPU 70 is, as stated above, a Z80 processor, and the PROM 74 is, for example, a 2764 dual in-line chip, the RAM 70 may be a TMM2016 P/D and the address decoder 92 an LS138 chip. A timer chip 120, for example, a 555 chip, is connected to provide a reset signal to the CPU 70 at an input 122, as well as to supply a reset signal to the bus 72. A bus frequency generator 124 includes an oscillator 126 connected to a clock input 128 of a high speed timer 130 which feeds two J-K flipflops 132 and 134 to generate a high speed bus frequency. The bus frequency in a preferred embodiment is twice the ultrasound frequency of the transducer 12, i.e. for a 1 MHz. ultrasound output, a 2 MHz. bus frequency is used. If an optional 3 MHz. transducer is used, a 6 MHz. bus frequency is used. The high speed timer 130 of one embodiment is an LS166A chip.

Figure 4B:
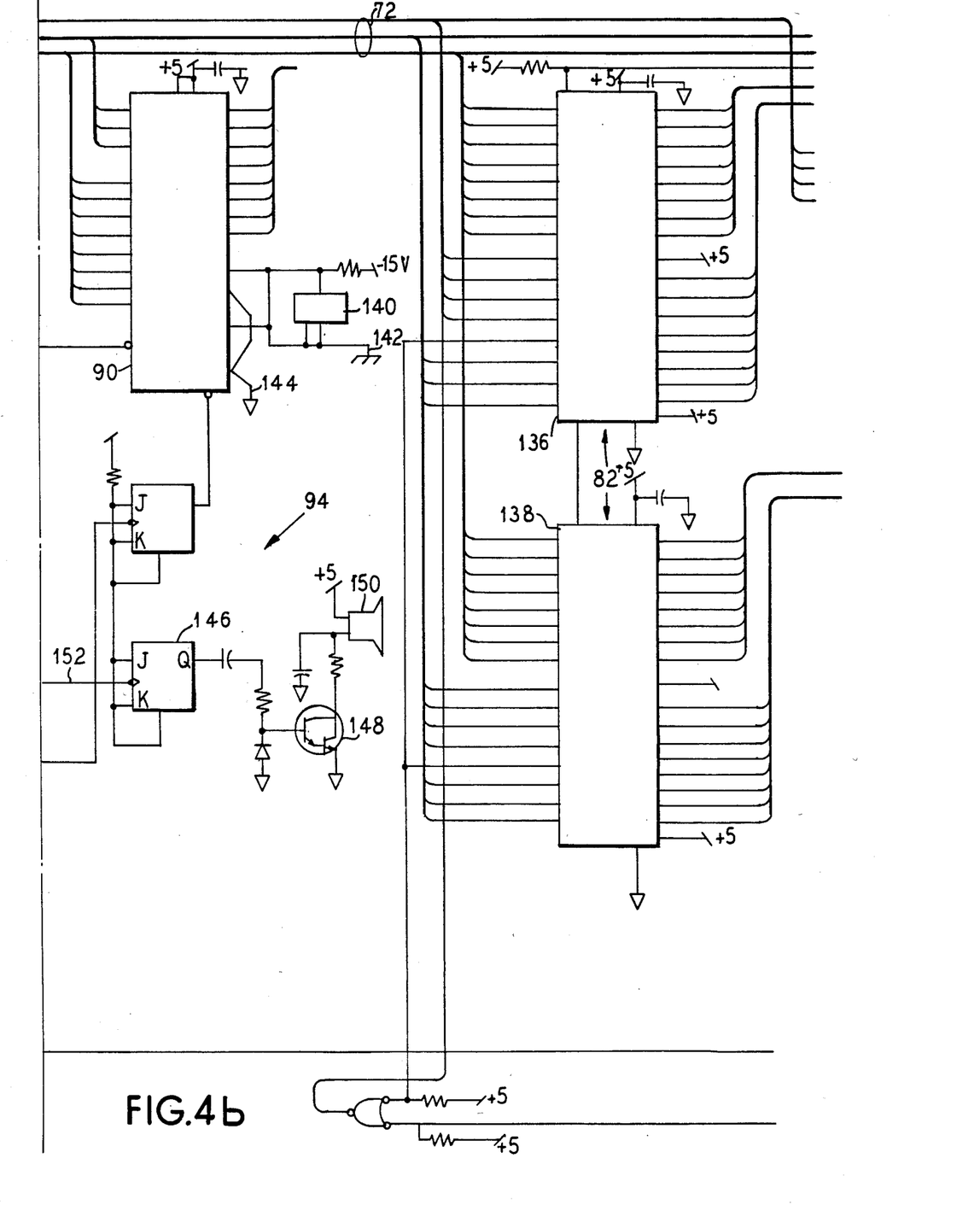

In FIG. 4b, the A/D converter 90 is, for example, a chip AD7581KN, while the two I/O ports 82 are shown as Z80 PIO integrated circuits 136 and 138. The A/D converter 90 is connected to a voltage reference element 140, which, for example, is an A6585J. Note that analog ground 142 is distinguished from digital ground 144 and the two are only connected at the A/D converter 90. A sound generator 94 is formed by a J-K flipflop 146 connected to a Darlington pair 148 which feeds a speaker 150. The sound generator 94 enables the microprocessor 70 to produce audio signals of any audible frequency. Each time the circuit is "addressed" over a sound lead 152 by the microprocessor 70, the flipflop 146 changes state and, since the flipflop 136 is capacitively coupled to drive the speaker 150, a momentary pulse of current is generated through the speaker 150 each time the flipflop 146 changes to a high logic state to cause the speaker cone to deflect and emit an audible click. For example, addressing the speaker 150 two thousand times per second produces an audible frequency of one KHz.

Figure 5:
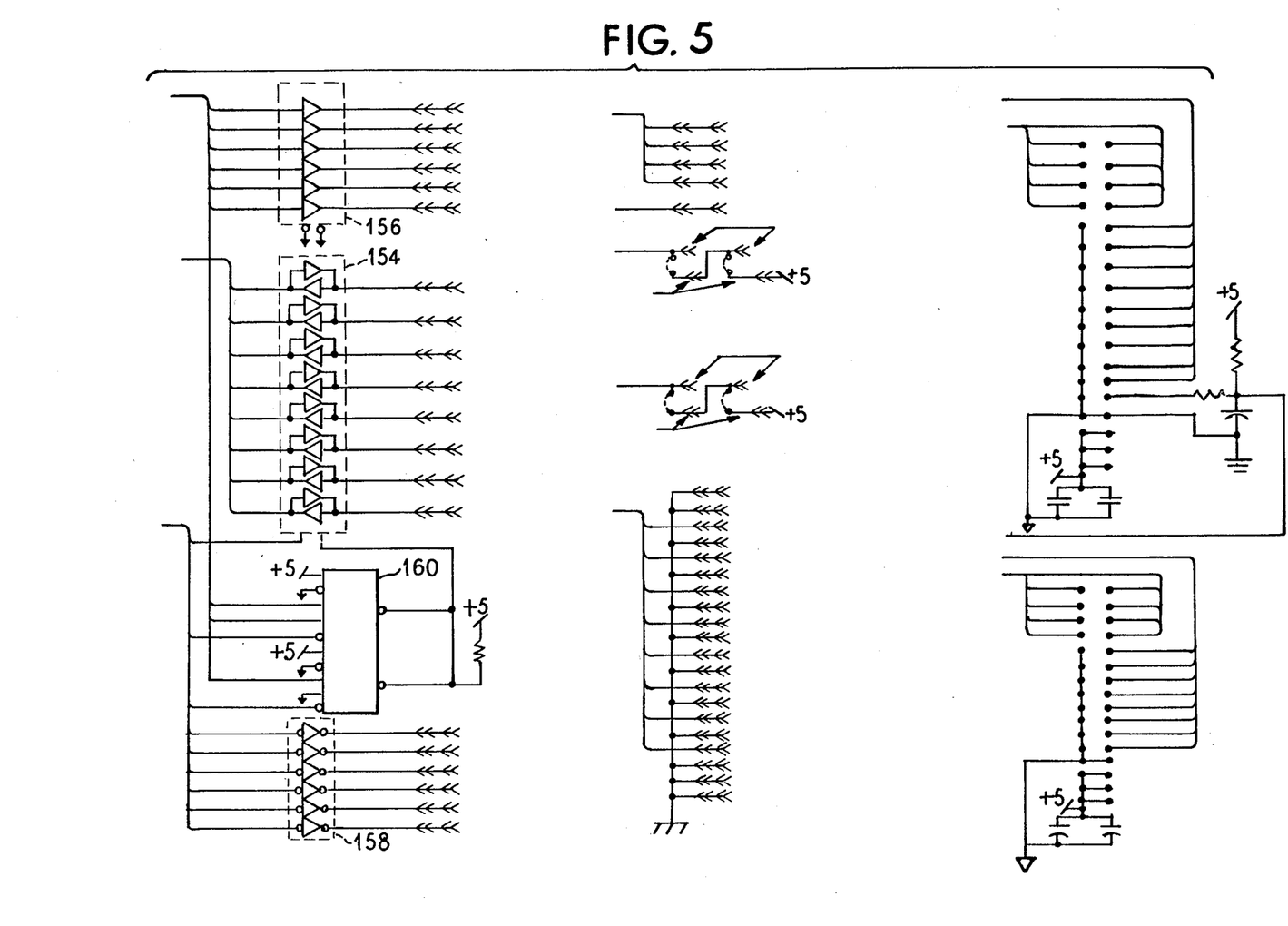

In FIG. 5, various pin interconnects for the control circuitry are shown, as well as a data buffer 154 and address buffers 156 and 158. A switching circuit 160, for example, an ALS539, is also included.

Figure 6:
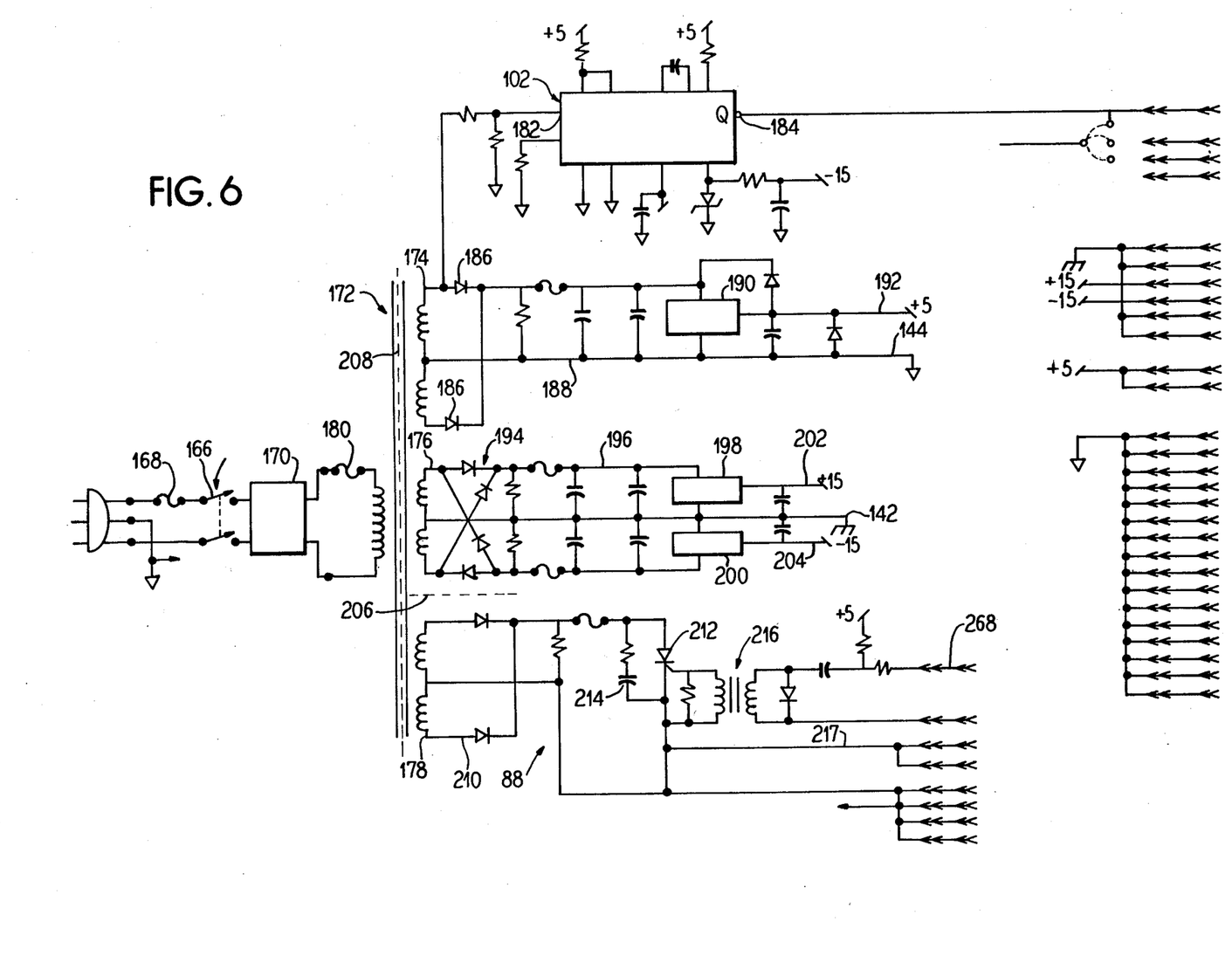

The power supply for the unit 10 is shown in FIG. 6, including the AC connector 26 and a double-pole single-throw power switch 166 connected by a fuse 168. A filter 170 is provided between the switch 166 and a main power transformer 172 that includes three secondary windings 174, 176, and 178. For added safety, a thermal cut-off 180 is mounted internally of the transformer 172. The first secondary winding 174 is connected to an input 182 of the zero crossing detector 102 which is formed by, among other things, an 8T20 integrated circuit chip. The zero crossing detector 102 is a bi-directional one shot which emits pulse from an output 184 at each zero axis crossing of the 60 Hz. power signal. Thus, the output at lead 184 is a 120 Hz. signal that is used for microprocessor program timing functions and which is sent to the counter timer circuit 86. The secondary winding 174, which in a preferred embodiment is a 15.7 volt RMS center tapped winding, is fed through diodes 186 and a filter arrangement 188 to a 5 volt integrated circuit regulator 190. The 5 volt regulator 190, which is, for example, an LM223AK, supplies a 5 volt DC signal between the 5 volt DC supply lead 192 and the digital ground 144.

The second secondary winding 176 of the main transformer 172, which is preferably a 31.8 volt RMS center tap winding, is fed through a full wave rectifier 194 and filtering elements 196 prior to being regulated by a pair of symmetrically connected 15 volt regulators 198 and 200. The voltage regulators 198 and 200 produce a +15 volt signal and a −15 volt signal, respectively, at the leads 202 and 204, between which is connected the analog ground 146. The voltage regulators 198 and 200 can be 78M15 and 79M15 integrated circuits, respectively.

The third secondary winding 178 of the main transformer 172 forms part of the SCR power supply 88 that supplies DC current to the ultrasound amplifier 84 which is used to produce the one MHz. ultrasound output signal. The winding 178 is preferably a 130 volt RMS center tapped winding and, since it forms part of the radio frequency portion of the circuit, it is shielded from the other secondary windings 174 and 176 by a shield 206. This is in addition to the usual Faraday shield 208 between the primary and secondary windings. A full wave rectifier 210 connects the secondary 178 to the anode of a silicon controlled rectifier (SCR) 212. The SCR 212 is normally in the off-state and no current flows through it to a filter capacitor 214. The SCR 212 is triggered by a signal from the counter timer circuit 86 through a transformer 216 and produces an output on lead 217.

In operation, each time the AC signal crosses the zero axis, the zero crossing detector 102 sends a pulse to the counter timer circuit 86. The counter timer circuit initiates a timing period which is established by the processors 70 and is based on the output intensity selected by the operator. The timing period of one embodiment ranges from 8.3 milliseconds to 4.15 milliseconds. The longer time period allows the entire AC half-wave to pass before the SCR 212 is fired and, thus, no energy passes through the SCR 212 to the filter capacitor 214. The shortest time period triggers the SCR 212 exactly when the half-wave is at its peak voltage. This produces the highest possible voltage on the filter capacitor 214. The capacitor 214 is large enough to store the energy needed by the ultrasound amplifier 84 through many cycles. Thus, the energy being pulsed into the filter capacitor 214 at a rate of 120 times per second is smoothed into a constant voltage and fed to the ultrasound amplifier 84.

Figure 7:
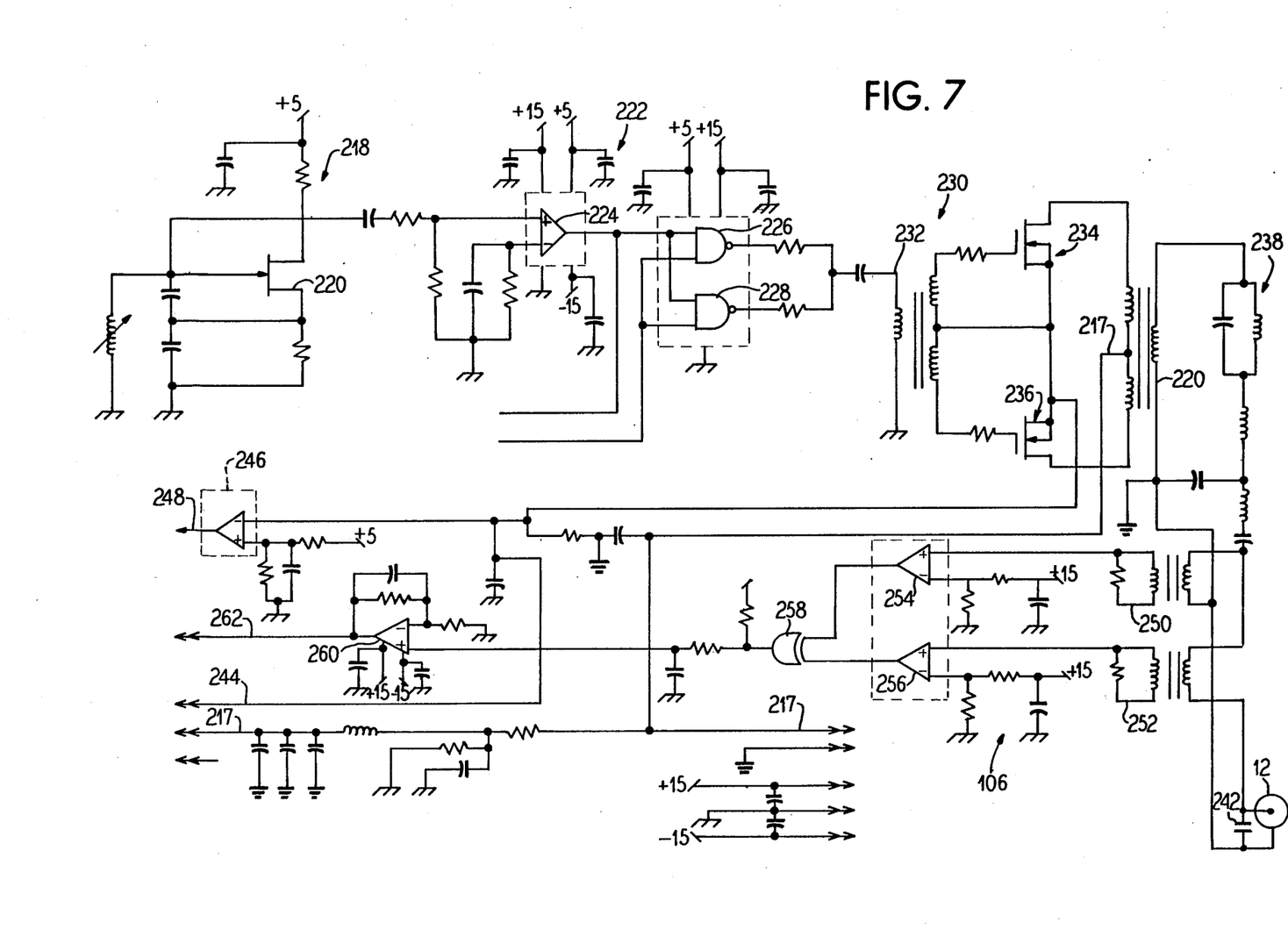

The ultrasound switching amplifier 84, which actually produces the ultrasound signal for transmission to the transducer 12, is shown in FIG. 7. Included is an oscillator portion 218, which is shown as a Colpitts oscillator having an FET 220. In place of a separate oscillator 218, the bus frequency signal may be used for the amplifier 84. The use of the processor circuit's timing signal as the frequency generator for the transducer 12 avoids the necessity of tuning the transducer 12 to the control circuit. The oscillator output, or alternately the bus frequency, is fed to a preamplifier 222 having an operational amplifier 224 and a pair of NAND logic gates 226 and 228.

A power amplifier portion 230 includes a transformer 232 with a center tapped secondary connected to a pair of high speed FETs 234 and 236. The FETs 234 and 236 are shown herein as insulated gate field effect transistors (IGFET). The two FETs 234 and 236 are alternately switched to saturation and to off, one FET being in a saturated state when the other FET is off. The resultant signal is a nearly square wave output. The power amplifier 230 is supplied with power through the lead 217 from the SCR 212 so that as the voltage on the lead 217 changes the amplitude of ultrasound output is hanged.

An output filter 238 is connected through a transformer 240 to the output of the power amplifier 210. The filter 238 is a two-stage filter which minimizes frequencies other than the desired one MHz. output frequency. Between the filter 238 and the transducer 12 is a power-factor correcting capacitor 242 that cancels the inductive component of the load and enables the transducer 12 to operate at a frequency midway between series resonance and parallel resonance for cooler and more efficient operation. The addition of the capacitor 242 also matches the impedance of the transducer 12 to the connecting cable to prevent standing waves and reduce noise.

Since the high speed FETs 234 and 236 are operated at either saturation or off, the operation of the switching amplifier 230 is very efficient. Little power is used by the amplifier 230 so that minimal heat sink devices are required and no fan is needed whatsoever. Very nearly all the power is supplied to the transducer crystal 12. In one embodiment, up to 20 watts of ultrasound energy is produced at the transducer 12.

The applied voltage lead 217 is sampled and sent to the A/D converter 90 for transmittal to the CPU 70. The current through the FETs 234 and 236 is likewise sampled on lead 244 for monitoring by the CPU 70. A comparitor 246 establishes a threshold level for the current and transmits an over current signal on lead 248 when the threshold is breached. Upon the over current condition being sensed, the unit 10 automatically shuts down.

Also in FIG. 7, the phase detector 106 includes a pair of small toroid transformers 250 and 252 connected to sample the voltage and current, respectively, at the, transducer load 12, while maintaining the transducer circuit in direct isolation. The voltage transformer 250 has a primary across the output of the filter 238 and the current transformer 252 has its primary winding in series with the output of the filter 238. The secondary windings of the transformers 250 and 252 are connected to comparison circuits 254 and 256, respectively, which convert the voltage and current sine waves to square waves of equal amplitude while maintaining their respective phase relationship. An exclusive OR logic gate 258 produces either a logic zero when the signals are instantaneously in phase, or a logic 1 when the signals are instantaneously out of phase. An operational amplifier 260 filters and integrates the output from the exclusive OR gate 258 to produce a voltage which reflects the relative phase difference between the voltage and current. This phase voltage is transmitted to the A/D converter 90 over lead 262 for use by the processor 70, from which, among other things, the degree of transducer/patient coupling is determined. If the processor through software senses that coupling has remained below a predetermined level for a set time, such as two seconds, the output power level is significantly reduced to prevent heating of the transducer 12.

Alternately, servoing can be accomplished by sensing the square of the power amplifier power supply voltage, or current, which is directly proportional to the ultrasound output acoustic power. Servoing here is also accomplished by software control of the processor.

Figure 8:
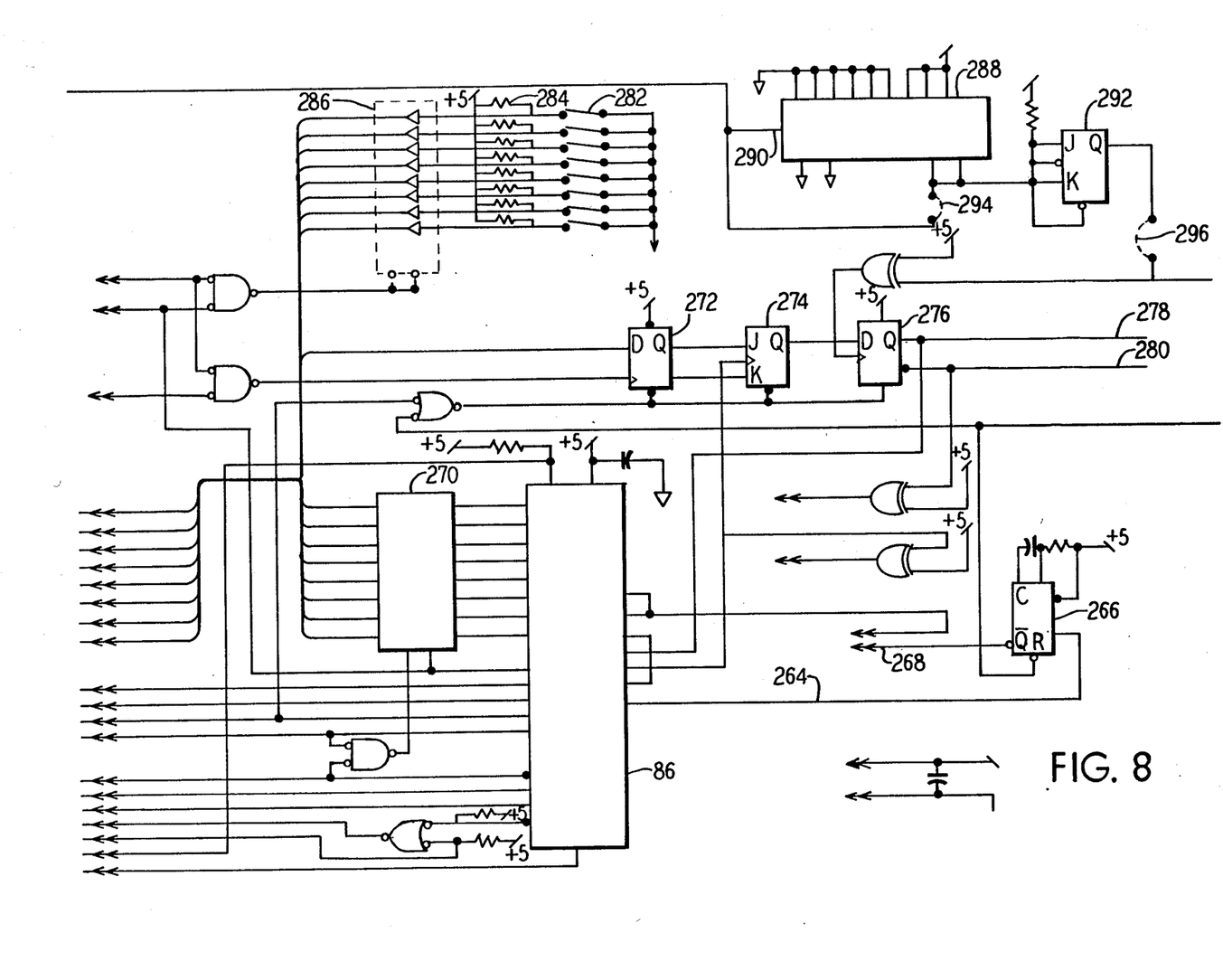

In FIG. 8, the counter timer circuit 86 is controlled by the processor 70 to initiate a timing period upon each zero crossing pulse from the zero crossing detector 102. The time delay pulse is transmitted on lead 264 to a flipflop 266, which generates trigger signal for the SCR 180 on lead 268 connected to the transformer 216. Two D flipflops 272, 276, and a J-K flipflop 274 are connected in series to generate on and off signals on the leads 278 and 280, respectively. A plurality of calibration switches 282 are operable to selectively ground data leads connected to a bank of pull-up resistors 284, which is connected to the CPU 70 through data buffers 286. A high speed timer 288 receives the bus frequency signal at a clock input 290 to strengthen the signal for transmittal through a J-K flipflop 292 and jumpers 294 and 296 to the balance of the control circuit.

Figure 9A:
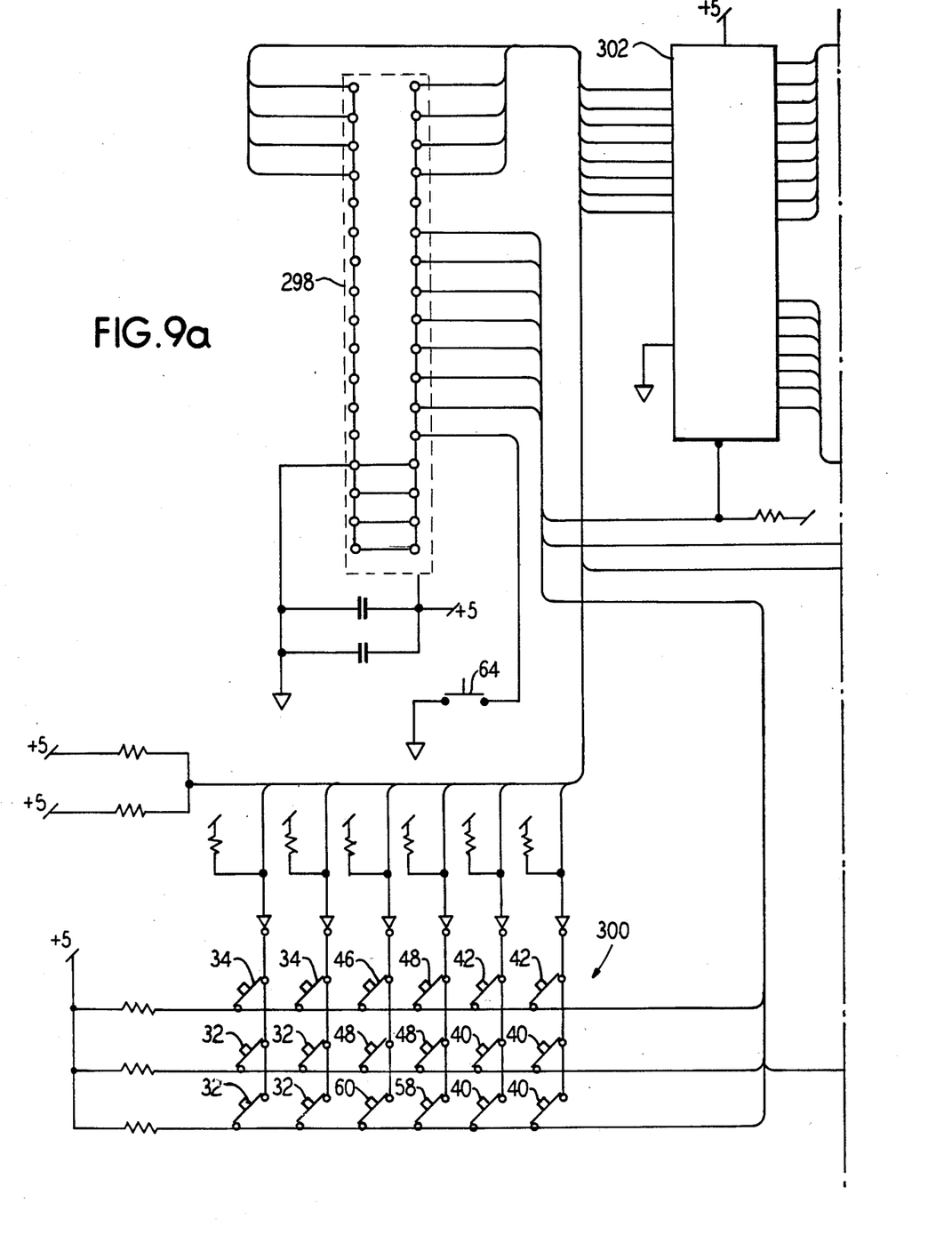
Figure 9B:
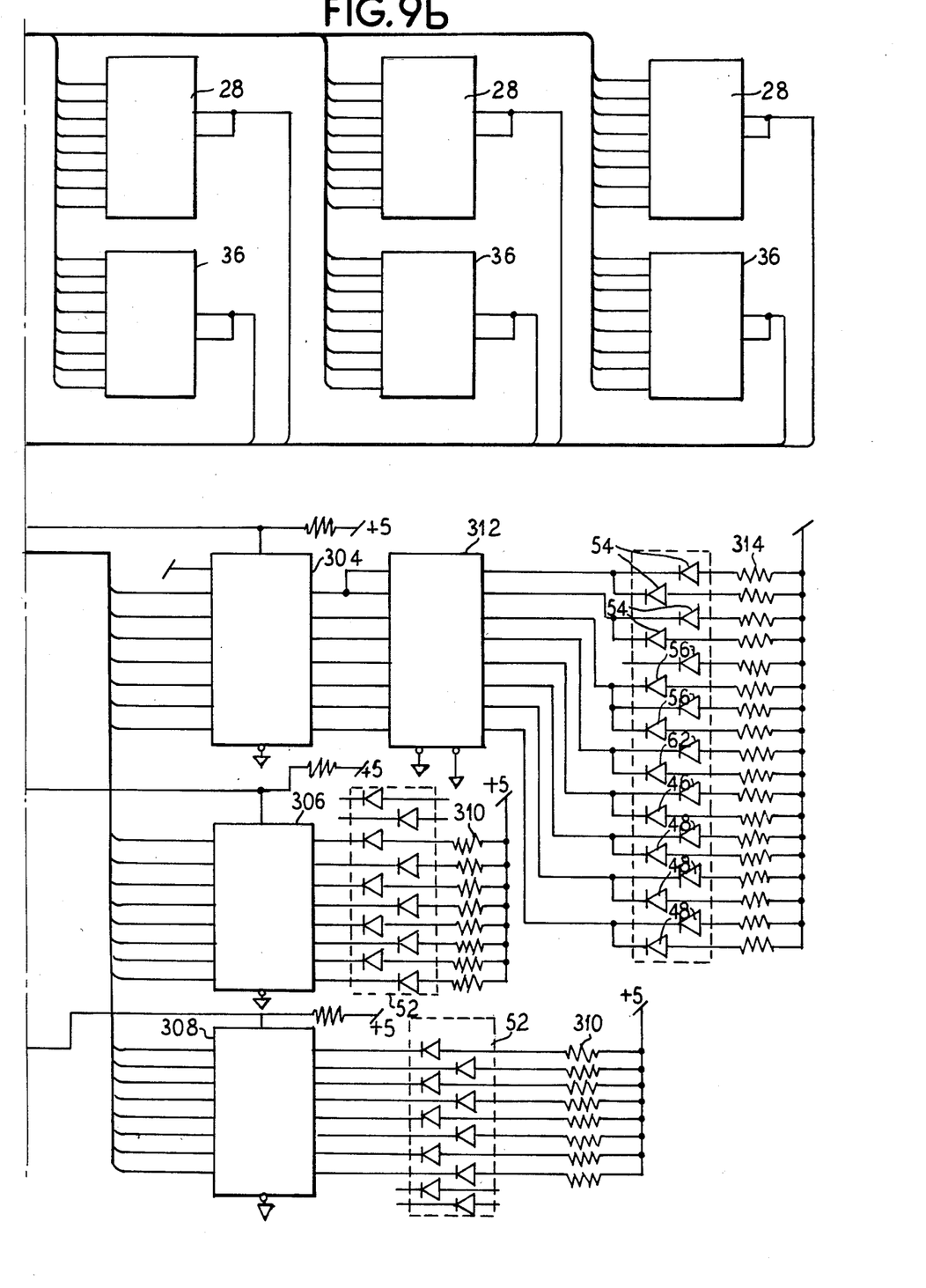

FIGS. 9a and 9b show the front panel circuitry, including a 34 pin header 298 for connection to the I/O ports 136 and 138. The reset switch 64 enables the operator to selectively place the circuitry in a known state.

A 3×6 matrix keypad 300 of SPST switches includes the rest of the front panel control switches 32, 34, 40, 42, 46, 48, 58, and 60. The switches are debounced and decoded by the microprocessor program. The I/O ports 136 and 138 provide an interface between the switches and the processor 70, the six columns being driven by the port 136 and the three rows being read by the port 138. Reading the keyboard 300 requires a series of program steps. First, the processor 70 writes a logic one to all columns and reads back the rows to see if any keys or switches are operated. If one is detected, the program waits a few milliseconds for the switch to stop bouncing and tries again. If a switch is still closed, the program enters a subroutine to determine by row and column which switch is pressed.

An LED driver 302 is also in FIG. 9a for driving the displays shown in FIG. 9b. The driver 302 preferably is an ICM 7218C1J1.

In FIG. 9b, six digit display elements correspond to the numeric displays 28 and 36 on the front panel 24 and are connected to the driver 302. A plurality of LEDs are also shown driven by latches 304, 306, and 308. The LEDs 52 form the coupling bar graph 50. Resistors 310 are connected to the LEDs 52.

A current boosting element 312, such as a 74LS244 integrated circuit, is connected between the latch 304 and the rest of the LEDs, which include resistors 314 and correspond to the output on display 54, the error display 56, the OK display 62, the continuous output display 46, and the pulse output displays 48. The displays are interfaced to the microprocessor 70 through the I/O ports 136 and 138 by transmitting the digit or LED information to the display by the port 136 and strobing the appropriate circuit through the other port 138.

Thus, there has been shown and described a therapeutic ultrasound device which provides a switching amplifier for generating an ultrasound signal, the amplifier being highly efficient and dissipating very little power in the form of heat. The present device also includes a phase detector which quantifies the phase relationship between the voltage and current at the transducer 12. The ultrasound transducer dynamically changes its impedance depending on the degree of coupling it makes with the patient's tissue. The changing impedance is easily determined from the instantaneous phase angle between the transducer voltage and the transducer current. The phase detector provides phase information to the processor 70 which, in addition to a voltage or current signal, enables the processor through software control to drive a visual coupling indicator, change output levels in response to varying tissue loads, and reduces output power to incidental levels when gross uncoupling occurs.

Alternately, the power amplifier supply current or voltage are used for servo control through the software in the microprocessor.

Another feature of the present invention is the coupling bar display 50 which shows the degree of coupling between the transducer and the patient for immediate correction by the therapist.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An ultrasound device for therapeutic application of ultrasound energy to a patient, comprising:
   a transducer means for placement in contact with a patient;
   a base unit connected for transmitting electrical signals to said transducer means;
   control means on said base unit for selectively controlling the transmission of signals to said transducer means;
   display means for showing the state of said control means and the electrical signal transmitted to said transducer means;
   means for connecting said base unit to AC electrical power;
   a control circuit in said base unit and connected to said control means and said display means, said control circuit including:
   an amplifier means for energizing said transducer means;
   a phase detector connected to monitor the phase difference between the current and voltage at said transducer means; and
   a programmed controller means connected to said phase detector and to said amplifier means for changing output power levels of said transducer means depending on the phase difference,
   whereby the phase difference varies as different tissues of the patient are coupled to said transducer means.

2. An ultrasound device as claimed in claim 1, wherein said amplifier means is a switching amplifier including a pair of active elements connected for mutually exclusive alternate saturation and off states.

3. An ultrasound device as claimed in claim 2, wherein said pair of active elements are high-speed field effect transistors.

4. An ultrasound device as claimed in claim 1, wherein said transducer means is a hand-held transducer removably connected to said base unit.

5. An ultrasound device as claimed in claim 1, wherein said display means includes a coupling display to show the portion of full coupling between said transducer means and patient.

6. An ultrasound device as claimed in claim 5, wherein said coupling display is a lighted bar graph for showing the fraction of coupling of said transducer means.

7. An ultrasound device as claimed in claim 1, further comprising:
   a zero crossing detector connected to AC power and having an output for carrying signals corresponding to no-voltage states of the AC power;
   a counter timer connected to said zero crossing detector output and having a trigger output, said counter timer controllable by said programmed controller to delay trigger signals on said trigger output following receipt of a no-voltage signal from said zero crossing detector; and
   a triggerable power supply connected to said trigger output, said triggerable power supply connected to control said amplifier means depending on the delay of said trigger signals;
   whereby said programmed controller controls the output signal level of said amplifier means to said transducer means through said counter timer.

8. An ultrasound device as claimed in claim 7, wherein said triggerable power supply includes a silicon-controlled rectifier.

9. An ultrasound device as claimed in claim 1, wherein said programmed controller means interrupts energy to said transducer means when said phase detector senses a phase difference greater than a predetermined amount for longer than a predetermined time.

10. An ultrasound device as claimed in claim 1, further comprising:
    a plurality of switches connected in said control circuit for calibrating said control circuit to match said transducer means.

11. An ultrasound device as claimed in claim 1, further comprising:
    a low voltage power supply for supplying power to portions of said control circuit;
    a main transformer connected in said control circuit to said AC power connecting means, said main transformer having a primary winding and at least two secondary windings;
    a first of said secondary windings connected to supply power to said amplifier means;
    a second of said secondary windings connected to said low voltage power supply; and
    a shield mounted between said first secondary and said second secondary of said main transformer to shield electrical signals at said first and second secondary windings from each other.

12. An ultrasound device as claimed in claim 1, wherein said display means includes a treatment time display and an output intensity display.

13. An ultrasound device as claimed in claim 1, further comprising:
    means for self-testing of said device upon power-up.

14. An ultrasound device as claimed in claim 1, further comprising: audible output means for producing an audible signal upon predetermined conditions.

15. An ultrasound device as claimed in claim 14, wherein said audible output means is driven by said programmed controller means.

16. An ultrasound device as claimed in claim 1, further comprising:
    a power factor correction capacitor connected to said transducer means so that said transducer is operable substantially midway between series resonance and parallel resonance.

17. An ultrasound device as claimed in claim 1, wherein said control means enables an operator to select treatment time, treatment intensity and duty cycle of ultrasound energy from said transducer means.

18. An ultrasound device as claimed in claim 1, wherein said programmed controller means includes a program for servo control of said transducer means energization.

19. An ultrasound device as claimed in claim 1, wherein the ultrasound energy emitted by said transducer means has a frequency of 1 MHz.

20. An ultrasound therapy device for applying ultrasound energy to a patient, comprising:
    a hand holdable transducer means having an applicator face for contact with the patient;

a flexible cable connected at a first end to said transducer means;

a power base unit connectable to a second opposite end of said cable, said base unit including a housing;

an AC power cord extending from said housing and connectable to AC power;

a front panel forming part of said housing, said front panel including operable controls and readable displays, said operable controls including:

means for setting treatment time of ultrasound energy from said transducer means;

means for setting the power of ultrasound energy from said transducer means; and means for selecting from continuous output energy and pulsed output energy from said transducer means, said selecting means including means to set one of a plurality of available pulse modes;

said readable displays including:

means for displaying treatment time set by said treatment time setting means, said time displaying means displaying remaining treatment time during treatments;

means for displaying power set by said power setting means, said power displaying means selectively displaying power per area from said applicator face during treatments; and means for displaying the portion of full coupling of ultrasound energy between said transducer means and the patient;

a control circuit in said housing connected to said operable controls and said readable displays, said control circuit including:

a programmed processor means for supervising the operation of said control circuit;

means for connecting said AC power cord to said control circuit, said connecting means including a transformer having at least two secondary windings inductively coupled to a primary winding connectable to AC power;

a zero crossing detector connected to a first of said secondary windings, said zero crossing detector generating a pulse at an output upon at least every other zero axis crossing of the AC power signal;

a counter timer connected to receive said zero crossing pulses from said zero crossing detector, said counter timer generating a trigger signal on a trigger lead for each zero crossing detection received, said counter timer controllable by said programmed processor to establish a predetermined delay between receipt of said zero crossing pulse and generation of said trigger signal;

a silicon controlled rectifier connected to a second one of said two secondary windings and having a trigger connected to said trigger lead, said silicon controlled rectifier setting a predetermined voltage level upon receipt of said trigger signal;

a filter element connectable to receive said predetermined voltage level from said silicon controlled rectifier;

a switching amplifier formed of a pair of active elements and connected to receive said predetermined voltage level from said filter element, said predetermined voltage level setting the output power at said transducer;

means for driving said switching amplifier at an ultrasound frequency, said driving means causing said pair of active elements to alternately and mutually exclusively switch between saturation and off;

an ultrasound frequency filter connected to filter unwanted frequencies from the output of said switching amplifier and to transmit the filtered signal to said transducer;

a phase detector connected to said transducer to monitor the voltage and the current at said transducer, said phase detector generating a signal representing the phase difference between said voltage and said current; and means for communicating said phase difference signal and said predetermined voltage level to said programmed processor;

whereby said programmed processor adjusts the ultrasound output energy depending on the phase difference signal and an electrical signal.

21. An ultrasound therapy device for therapeutic application of ultrasound energy to a patient, comprising:

a transducer means for placement in contact with a patient;

a base unit connected to transmit electrical signals to said transducer means;

control means on said base unit for selectively controlling the transmission of signals to said transducer means;

display means for showing the state of said control means and the electrical signal transmitted to said transducer means;

means for connecting said base unit to AC electrical power;

a control circuit in said base unit and connected to said control means and said display means, said control circuit control including:

an amplifier means for energizing said transducer means, and a power supply connected to supply power to said amplifier means; and a programmed controller means connected to said amplifier means and to said power supply for changing output power levels of said transducer means depending on a square of a supply signal to said power supply, whereby said square of said supply signal varies as different tissues of the patient are coupled to said transducer means.

* * * * *